(12) United States Patent
Remer et al.

(10) Patent No.: US 6,484,726 B1
(45) Date of Patent: *Nov. 26, 2002

(54) ARTICULATING EARPLUG

(75) Inventors: Dean M. Remer, Woodbury; Paul A. Martinson, Maplewood, both of MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/608,911

(22) Filed: Jun. 30, 2000

(51) Int. Cl.$^7$ ............................................... A61F 11/00
(52) U.S. Cl. ........................................ 128/864; 128/865
(58) Field of Search ................................ 128/864–868; 181/129, 130, 135

(56) References Cited

U.S. PATENT DOCUMENTS

| | | | |
|---|---|---|---|
| 2,446,707 A | 8/1948 | Leight | 128/152 |
| 2,487,038 A | 11/1949 | Baum | |
| 2,538,339 A | 1/1951 | Thomas | 128/151 |
| 2,804,072 A | 8/1957 | Genzer | 128/152 |
| 2,850,012 A | 9/1958 | Becker | |
| 3,131,241 A | 4/1964 | Mendelson | 264/257 |
| 3,811,437 A | 5/1974 | Gardner | 128/152 |
| D242,743 S | 12/1976 | Leight | D83/1 |
| 4,094,315 A | 6/1978 | Leight | 128/152 |
| 4,490,857 A | 1/1985 | Leight et al. | 2/209 |
| 4,582,053 A | 4/1986 | Wilson | |
| 4,671,265 A | 6/1987 | Andersson | 128/152 |
| 4,819,624 A | 4/1989 | Leight et al. | 128/866 |
| 5,044,463 A | 9/1991 | Carr | 181/135 |
| D340,282 S | 10/1993 | Leight | D24/106 |
| D358,463 S | 5/1995 | Falco | D24/106 |
| D371,193 S | 6/1996 | Myers et al. | D24/106 |
| 5,701,348 A | 12/1997 | Shennib et al. | |

FOREIGN PATENT DOCUMENTS

| | | |
|---|---|---|
| GB | 2021908 | 10/1992 |
| JP | 10314213 | 2/1998 |
| WO | WO 99/36016 | 7/1999 |

OTHER PUBLICATIONS

U.S. Des. application Ser. No. 29/132,306, filed Nov. 6, 2000, entitled Earplug, inventors Remer et al.
U.S. Des. application Ser. No. 29/132,307, filed Nov. 6, 2000, entitled Earplug, inventors Remer et al.

*Primary Examiner*—Michael A. Brown
(74) *Attorney, Agent, or Firm*—KArl G. Hanson; Allison Johnson

(57) ABSTRACT

A foam earplug that includes a first segment a second segment and a predetermined articulation zone disposed between the first segment and the second segment. The earplug exhibits an equilibrium bend force of no greater than about 10 g.

31 Claims, 3 Drawing Sheets

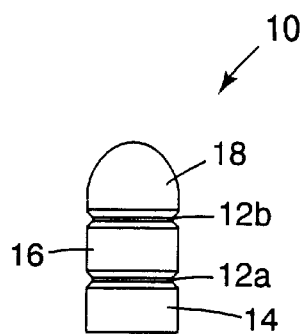
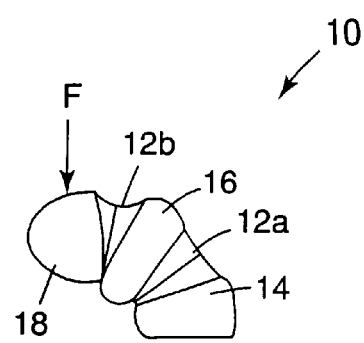
Fig. 1a  Fig. 1b
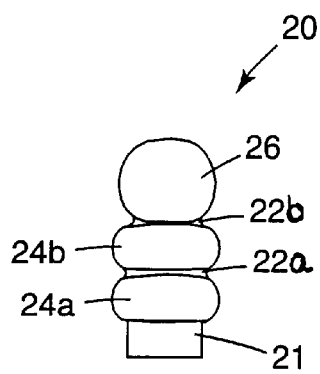
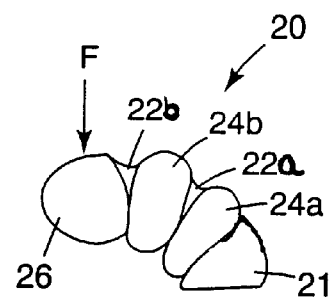
Fig. 2a  Fig. 2b
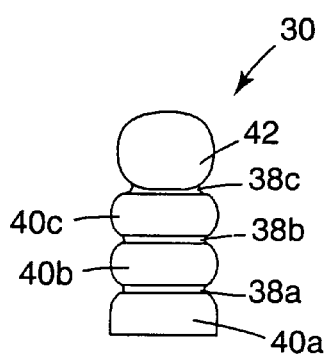
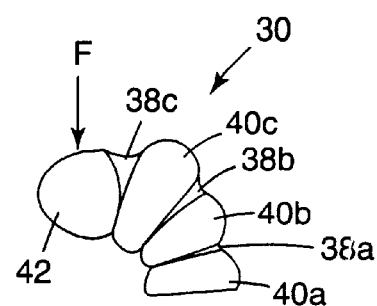
Fig. 3a  Fig. 3b

ARTICULATING EARPLUG

BACKGROUND

The invention relates to articulating earplugs.

Earplugs have been used for many years to protect hearing. Over the years earplugs have been made from a variety of different materials including cotton, soft wax, thermoplastic polymers and foam. The shape of earplugs has also been varied to achieve improved effectiveness and comfort. Examples of known earplugs are disclosed in U.S. Pat. Nos. 4,094,315, 5,044,463, Des. 340,282, Des. 358,463, and Des. 371,193 and examples of known banded earplugs are disclosed in U.S. Pat. Nos. 4,490,857, 4,819,624, and 4,671,265.

A person's ear canal has a number of bends and a diameter changes located along the path of the canal. Good hearing protection can generally be obtained if the earplug is inserted just past the first bend of the canal. The bending of an earplug in the canal, however, can cause a force to be exerted on the canal, which creates discomfort for the wearer. The resulting irritation may cause the wearer to pull the plug out of the ear, either totally or partially. Wearers thus must endure the pain and discomfort caused by such an earplug or risk exposing their ears to loud noises that can damage their hearing.

SUMMARY OF THE INVENTION

The present invention is directed to a new earplug that can protect the wearer from loud noises without causing serious discomfort to the wearer.

In brief summary, the invention features a foam earplug that includes a first segment, a second segment, and a predetermined articulation zone disposed between the first segment and the second segment, such that the earplug exhibits an equilibrium bend force of no greater than about 10 g.

In another aspect the invention features a foam earplug that includes a first segment, a second segment, and a predetermined articulation zone disposed between the first segment and the second segment and adjacent the first segment and the second segment, the cross sectional area of the earplug taken at the articulation zone being no greater than about 80% of the cross sectional area of the earplug taken at the apex of the first segment and no greater than about 80% of the cross sectional area of the earplug taken at the apex of the second segment.

The inventive earplug is capable of bending at least one predetermined zone to exert a relatively low force against the inner wall of the ear canal. The earplug can be constructed to include a number of predetermined articulation zones, which can enable the earplug to bend in a number of different directions, and which can enable the segments to move somewhat independently relative to one another. The earplug can adapt to the contours of the ear canal and obturate the ear canal. In short the inventive earplug may provide good comfort to the wearer as well as good hearing protection.

GLOSSARY

In reference to the invention, these terms have the meanings set forth below:

"Articulated" means composed of segments.

"Articulating" refers to jointed bending.

"Articulation zone" is a joint that is capable of being bent.

"Predetermined articulation zone" is an articulation zone that is created when the earplug is manufactured.

Other features and advantages of the invention will be apparent from the following description of the preferred embodiments thereof, and from the claims.

BRIEF DESCRIPTION OF THE DRAWINGS

FIG. 1a is a side view of one embodiment of an earplug 10 that includes articulation zones 12a, 12b.

FIG. 1b is a side view of the earplug 10 of FIG. 1a in a bent position.

FIG. 2a is a side view of a second embodiment of an earplug 20 that includes articulation zones 22a, 22b, 22c.

FIG. 2b is a side view of the earplug 20 of FIG. 2a in a bent position.

FIG. 3a is a side view of a third embodiment of an earplug 30 that includes articulation zones 38a, 38b, 38c.

FIG. 3b is a side view of the earplug 30 of FIG. 3a in a bent position.

DETAILED DESCRIPTION OF THE PREFERRED EMBODIMENTS

Figure 4:
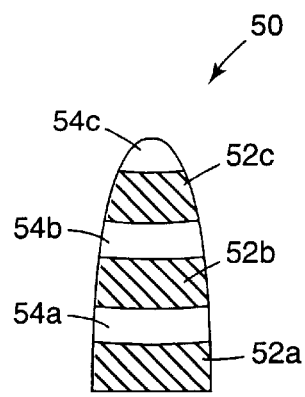
FIG. 4 is a side view of an earplug 50 according to a fourth embodiment.

The earplug preferably exhibits an equilibrium bend force (i.e., the force required to maintain the earplug in a bent position) of no greater than about 10 g, more preferably no greater than about 6 g, when tested according to the Equilibrium Force Test Method. The earplug also preferably exhibits a peak bend force (i.e., the greatest force required to bend the earplug) of no greater than about 30 g, more preferably no greater than about 20 g, when tested according to the Peak Force Test Method.

Preferably the earplug is resiliently deformable such that, once compressed or deformed, it expands to its original shape in the absence of a countering force. Thus, the earplug can be deformed or compressed for insertion into the ear canal, and, once inserted, the earplug will recover (e.g., expand) sufficiently to effectively obturate the ear canal.

Preferably the earplug is constructed such that the cross sectional area of the earplug taken at an articulation zone is no greater than about 80%, more preferably no greater than about 75%, most preferably no greater than 70%, of the cross sectional area of the earplug taken at the apex (i.e., the greatest cross sectional dimension) of each of the two segments that are adjacent the articulation zone and that define the predetermine articulation zone.

FIGS. 1–9 depict earplugs according to a number of different embodiments. FIGS. 1a and 1b illustrate an earplug 10 that includes a predetermined articulation zone 12a disposed between a first segment 14 and a second segment 16, and a second predetermined articulation zone 12b disposed between second segment 16 and an arcuate end segment 18, as shown in FIG. 1a. When a force (F) is exerted on the earplug 10, the earplug 10 ends at least one of the predetermined articulation zones 12a, 12b, as shown in FIG. 1b.

The earplug can include any number of articulation zones separated by segments. Preferably the earplug includes at least two predetermined articulation zones, more preferably at least three predetermined articulation zones.

FIGS. 2a and 2b show an earplug 20 that includes a substantially cylindrical end segment 21, a first predetermined articulation zone 22a disposed between first segment 24a and second segment 24b, and a second predetermined articulation zone 22b disposed between the second segment 24b and a substantially spherical end segment 26.

The predetermined articulation zone(s) and the segments can extend in a continuous or discontinuous band around the circumference of the earplug and can be of a variety of shapes and dimensions. An articulation zone or a segment, when taken in cross-section, may define a variety of shapes including, e.g., a circle, ellipse, and multi-faced shapes including, e.g., triangle, square, and rectangle. A segment may also be arcuate, spherical or cylindrical. In some embodiments, e.g., the distal end segment is cylindrical, flared, or curved and the proximal end is spherical or arcuate. A segment may be in the form of a continuous or discontinuous protuberance having an exterior wall that is curved (e.g., convex), flat, or a combination thereof Examples of protuberances having curved exterior walls include circular and elliptical protuberances. Examples of protuberances that have a flat exterior wall include tetragonal (e.g., square, rectangular and rhombohedral), hexagonal and frustoconical protuberances, and protuberances that are truncated forms thereof. The predetermined articulation zone(s) and the segments are preferably dimensioned such that they cooperate with each other to enable the segments of the earplug to bend, expand and contract somewhat independently of one another (i.e., in a segmented fashion).

FIGS. 3a and 3b illustrate an earplug 30 that includes three predetermined articulation zones 38a, 38b and 38c, three segments 40a, 40b and 40c (segments 40a and 40b each form of a convex protuberance), and a substantially spherical proximal end segment 42.

The earplug can be a unitary member that consists of or consists essentially of a single or homogeneous material. The earplug can also include articulation zone(s) and segments that differ in at least one property relative to each other, such as density, hardness, stiffness or a combination thereof. By altering one of these properties of at least one segment that borders an articulation zone(s) such that the segment has a higher density or greater hardness or stiffness relative to the articulation zone, the earplug exhibits a propensity to bend at the predetermined articulation zone when a force is exerted against the earplug.

A difference in density, hardness or stiffness of portions of the earplug can be achieved using a variety of techniques. The earplug can be constructed from a number of different materials having different properties such that the segments, the articulation zone(s), the body of the earplug, or a combination thereof are of a different material. For example, the segments can be made of a first material and the articulation zone(s) can be made of a second material, where at least one property selected from the group consisting of hardness, density or stiffness of the first material differs from (i.e., is greater than) that property in the second material. The difference between the property(s) of the first material and the second material creates the propensity of the earplug to bend at the articulation zone. In FIG. 4, for example, the earplug 50 includes segments 52a, 52b and 52c of a first material. These segments alternate with predetermined articulation zones 54a, 54b and 54c of a second material.

The earplug can also include a film, e.g., a coating or a skin, on a region (e.g., a segment, an articulation zone or a combination thereof) of the earplug. The film can be continuous or discontinuous and can extend around the circumference of the earplug or exist in a discrete portion of a region. The film can alter the properties of the region with which it is associated. For example, the film can render the film-covered region (e.g., a segment) stiffer relative to a film-free region (e.g., an articulation zone) of the earplug. Increasing the film thickness can increase the stiffness of the region. The film can include the composition of the earplug, a composition that differs from the earplug composition, or a combination thereof.

The film can be formed by applying, e.g., coating, a composition, e.g., a thermoplastic composition, on the earplug. The composition can penetrate into the body of the earplug. The distance the composition penetrates into the depth of the body of the earplug, e.g., into the pores of a foam body, and the relative properties, e.g., density, hardness, stiffness or a combination thereof, of the coated composition can alter the properties of the film-covered region, e.g., increasing the distance the composition travels into the depth of a region can result in an increase in the stiffness of the region.

The film can also be in the form of a skin formed on the exterior of the earplug. One method of forming a skin includes injecting the earplug material into a mold cavity such that a skin of the earplug material forms on the exterior of the earplug. The thickness of the skin can be altered during processing, e.g., by altering the temperature of various regions of the mold while the earplug material is present in the mold cavity. For some molding compositions, decreasing the mold temperature will cause an increase in skin thickness.

Figure 5:
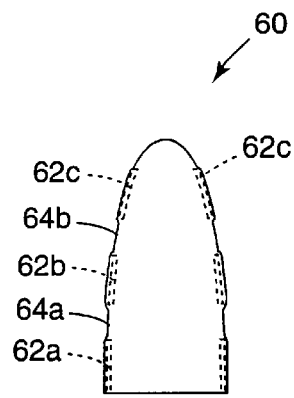
FIG. 5 is a view taken in cross section of an earplug 60 according to a fifth embodiment.

The earplug 60 depicted in FIG. 5 includes a layer of film 68 on segment surfaces. The film-covered segments 62a, 62b and 62c are stiffer relative to the film-free articulation zones 64a and 64b such that the earplug 60 exhibits a propensity to bend at an articulation zone 64a, 64b when a force is exerted on the earplug 60.

In other embodiments, the earplug includes a core element embedded in a matrix, e.g., foam, as shown in FIGS. 6–9. The core element can be of a variety of shapes and sizes including, e.g., spherical, cylindrical, circular, elliptical, triangular, square, or rectangular. The core element is preferably stiffer relative to the surrounding matrix. Preferably the core element is a foam or plastic.

Figure 6:
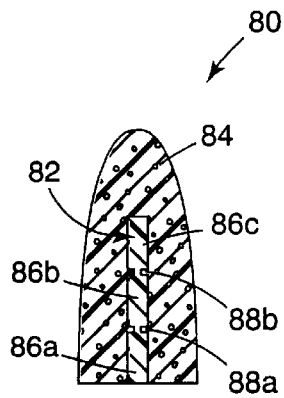
FIG. 6 is a side view of an earplug 80 that includes a core 82 according to a sixth embodiment.
Figure 7:
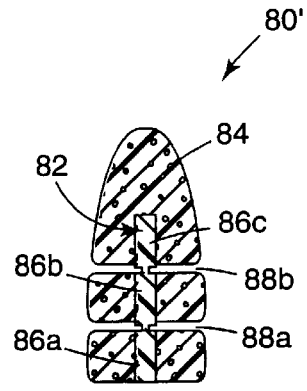
FIG. 7 is a side view of an earplug 80' according to a seventh embodiment.

FIGS. 6 and 7 show earplugs 80 and 80', respectively, that include a cylindrical core element 82 that is embedded in matrix 84. Matrix 84 includes segments 86a, 86b, and 86c, which each have a first, larger diameter and articulation zones 88a, 88b having a second, smaller diameter. The relatively smaller diameter articulation zones 88a, 88b have a greater propensity to bend under the influence of a force relative to the larger diameter segments 86a, 86b and 86c.

As illustrated in FIG. 7, the earplug 80' can include a core element 82 that includes core segments 86a and 86b, and 86c surrounded by matrix 84, and articulation zones 88a and 88b that are free of surrounding matrix 84.

Figure 8:
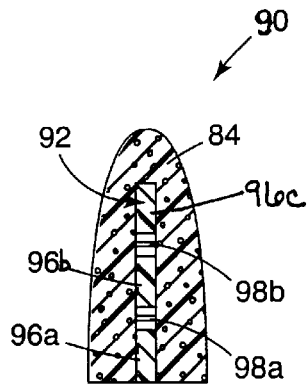
FIG. 8 is a side view of an earplug 90 according to a eighth embodiment.

In another embodiment, shown in FIG. 8, the earplug 90 includes a core element 92 that includes segments 96a, 96b and 96c and articulation zones 98a and 98b made from different materials (e.g., materials of different density, hardness, stiffness or a combination thereof). The material of the articulation zones 98a and 98b is such that the earplug 90 will exhibit a greater propensity to bend at the articulation zones 98a and 98b relative to the segments 96a, 96b and 96c.

Figure 9:
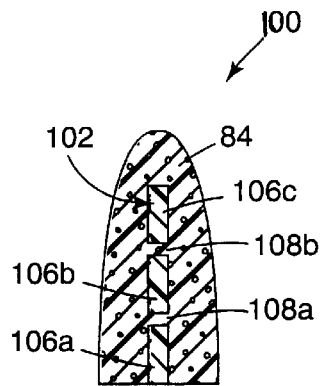
FIG. 9 is a side view of an earplug 100 according to an ninth embodiment.

In some embodiments, illustrated, e.g., in FIG. 9, the core element 102 is discontinuous such that the core element 102 includes segments 106a, 106b and 106c spaced apart form each and separated from each other by the surrounding matrix 104 of the body of the earplug 100. The areas between the segments 106a, 106b and 106c form the articulation zones 108a and 108b.

The invention will now be described further by way of the following examples.

EXAMPLES

Test Procedures

The test procedures used in the examples were as follows.

Peak Bend Force Test Method

Figure 10:
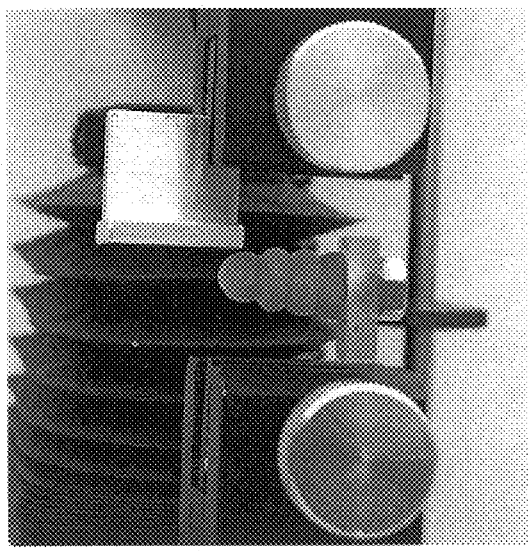
FIG. 10 is a side view of the earplug positioned horizontally in a Bend Force Test Apparatus.
Figure 11:
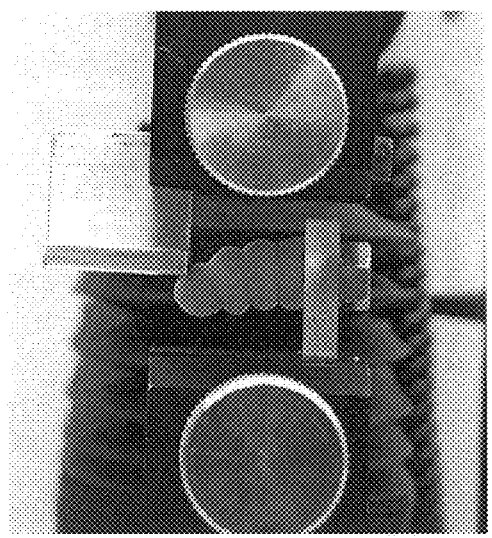
FIG. 11 is a side view of a force being exerted on the earplug of FIG. 10.

The base (i.e., distal) end of an earplug is coated with an adhesive composition and then adhered to a metal substrate. The metal substrate is positioned such that the longitudinal extent of the earplug extends horizontally from the metal substrate as illustrated in FIG. 10. A probe consisting of a 25 mm×25 mm aluminum plate positioned perpendicular to the length of the plug, as illustrated in FIG. 10, is attached to a force measuring device that records force measurements at a rate of 10 measurements per second. The probe moves vertically along a linear path into contact with the earplug at a point 2 cm from the base of the earplug, as illustrated in FIG. 11. Once contact with the earplug is made, the probe moves vertically an additional 5.7 mm at a rate of 3 mm/second, thereby bending the plug. The peak bend force (g) that is reached is then recorded. The peak bend force test is conducted at room temperature (about 22° C. (72° F.)).

Equilibrium Bend Force Test Method

After the peak bend force is obtained, the probe holds the position for 30 seconds. During this period, the force required to maintain the earplug in the bent position degrades to an equilibrium force. The equilibrium bend force is determined by measuring the force exerted on the earplug at rate of 10 measurements/second during the period from 20.0 seconds to 29.9 seconds and taking an average of the values obtained. The equilibrium bend force (g) is then recorded. The equilibrium bend force test is conducted at room temperature (about 22° C. (72° F.)).

EXAMPLE 1

An earplug foam-forming composition was prepared as follows. 37 parts isocyanate prepolymer including: 66.3% toluene diisocyanate, 17.5% polypropylene glycol (2000 molecular weight), 16.2% tripropylene glycol (Dow, Midland, Mich.); 40 parts of a blend of Voranol polyols including 16.67% type 2110 polyol, 16.67% type 2120 polyol, 16.67% type 3701 polyol, 48.33% type 450N polyol, and 1.67% type 1421 polyol (Dow, Midland, Mich.; 0.37 parts Dabco DC198 surfactant (Air Products, Allentown, Pa.); 0.86 parts Fomrez C-2 stannous octoate catalyst (Witco, Houston, Tex.); 0.13 parts inert pigment; and 0.24 parts water.

The earplug foam-forming composition was poured into molds and allowed to react to form foam earplugs of the shape shown in FIG. 2a. The foam earplugs were nominally 25 mm long with a flat end portion.

The foam earplugs were tested according the Test Procedures set forth above. The results are reported in Table 1.

EXAMPLE 2

The earplug foam-forming composition of Example 1 was poured into molds and allowed to react to form foam earplugs of the shape depicted in FIG. 3a. The foam earplugs were nominally 25 mm long with a flat end portion.

The foam earplugs were tested according the Test Procedures set forth above. The results are reported in Table 1.

TABLE 1

| Example | Peak Force (g) | Equilibrium Force (g) |
| --- | --- | --- |
| 1 | 9.436 | 3.556 |
| 2 | 9.932 | 4.152 |

All patents and patent applications cited in this document, including those cited in the Background, are incorporated by reference in total.

This invention may be suitably practiced in the absence of any element not explicitly described in this document.

Other embodiments are within the claims.

What is claimed is:

1. A foam earplug comprising:
   a first segment;
   a second segment; and
   a predetermined articulation zone disposed between the first segment and the second segment such that the earplug exhibits an equilibrium bend force of no greater than about 10 g.

2. An earplug according to claim 1, which earplug exhibits a peak bend force of no greater than about 30 g.

3. The earplug of claim 1, wherein the first segment comprises a protuberance, the protuberance being circular, elliptical, triangular, tetragonal, hexagonal, or frustoconical.

4. The earplug of claim 3, wherein the second segment comprises a convex protuberance.

5. The earplug of claim 1, further comprising a substantially spherical end segment.

6. The earplug of claim 5, further comprising a second predetermined articulation zone disposed between the substantially spherical end segment and the first segment.

7. The earplug of claim 1, further comprising a cylindrical end segment.

8. The earplug of claim 1, further comprising a third segment and a second predetermined articulation zone disposed between the third segment and the second segment.

9. The earplug of claim 8, wherein the third segment is cylindrical.

10. The earplug of claim 8, wherein the first segment comprises a convex protuberance, the second segment comprises a convex protuberance, and the third segment comprises a substantially spherical protuberance.

11. The earplug of claim 10, further comprising a fourth segment adjacent the first segment.

12. The earplug of claim 11, wherein the fourth segment comprises a convex protuberance.

13. The earplug of claim 11, wherein the fourth segment is cylindrical.

14. The earplug of claim 8, wherein the first segment comprises a convex protuberance, the second segment comprises a convex protuberance, and the third segment is cylindrical.

15. The earplug of claim 1, wherein the first segment has at least one property selected from the group consisting of density, hardness, stiffness or a combination thereof, that differs from the corresponding property of the articulation zone.

16. The earplug of claim 1, further comprising a film disposed on the first segment.

17. The earplug of claim 1, further comprising a core element, the core element being embedded in a foam matrix.

18. The earplug of claim 17, wherein the core element comprises the first segment and the second segment.

19. The earplug of claim 17, wherein the core element comprises foam.

20. The earplug of claim 19, wherein the density of the foam of the core element is greater than the density of the foam matrix.

21. The earplug of claim 17 wherein the core element comprises a first material and a second material.

22. The earplug of claim 17, wherein the core comprises plastic.

23. The earplug of claim 17, wherein the core element comprises a cylindrical portion.

24. The earplug of claim 17, wherein the core element comprises a cylinder comprising a first region having a first diameter and a second region having a second diameter, said first diameter being different from said second diameter.

25. An earplug according to claim 1, wherein the earplug comprises a unitary member.

26. An earplug according to claim 1, the earplug being capable of obturating sound when inserted into the ear canal of a user.

27. A foam earplug that comprises:
   a first segment;
   a second segment; and
   a predetermined articulation zone disposed between the first segment and the second segment and adjacent the first segment and the second segment,
   the cross sectional area of the earplug taken at the articulation zone being no greater than about 80% of the cross sectional area of the earplug taken at the apex of the first segment and no greater than about 80% of the cross sectional area of the earplug taken at the apex of the second segment.

28. The foam earplug of claim 27, wherein the cross sectional area of the earplug taken at the articulation zone is no greater than about 75% of the cross sectional area of the earplug taken at the apex of the first segment.

29. The foam earplug of claim 27, wherein the cross sectional area of the earplug taken at the articulation zone is no greater than about 70% of the cross sectional area of the earplug taken at the apex of the first segment.

30. The earplug of claim 27, wherein the earplug exhibits an equilibrium bend force of no greater than about 10 g.

31. The earplug of claim 27, wherein the earplug exhibits a peak bend force of no greater than about 30 g.

* * * * *